(12) United States Patent
Ottinger et al.

(10) Patent No.: US 11,578,634 B2
(45) Date of Patent: Feb. 14, 2023

(54) OPTICAL SENSING OF $NO_x$ AND AMMONIA IN AFTERTREATMENT SYSTEMS

(71) Applicant: CUMMINS EMISSION SOLUTIONS INC., Columbus, IN (US)

(72) Inventors: Nathan A. Ottinger, Lenoir City, TN (US); Z. Gerald Liu, Madison, WI (US); Yuanzhou Xi, Verona, WI (US)

(73) Assignee: Cummins Emission Solutions Inc., Columbus, IN (US)

( * ) Notice: Subject to any disclaimer, the term of this patent is extended or adjusted under 35 U.S.C. 154(b) by 0 days.

(21) Appl. No.: 17/743,589

(22) Filed: May 13, 2022

(65) Prior Publication Data

US 2022/0268195 A1 Aug. 25, 2022

Related U.S. Application Data

(62) Division of application No. 17/277,900, filed as application No. PCT/US2019/045931 on Aug. 9, 2019, now abandoned.

(Continued)

(51) Int. Cl.
*F01N 3/20* (2006.01)
*F01N 9/00* (2006.01)
(Continued)

(52) U.S. Cl.
CPC ............ *F01N 3/2066* (2013.01); *F01N 9/00* (2013.01); *F01N 11/00* (2013.01); *G01N 21/33* (2013.01);
(Continued)

(58) Field of Classification Search
CPC .......... F01N 3/2066; F01N 9/00; F01N 11/00; F01N 3/106; F01N 2560/021;
(Continued)

(56) References Cited

U.S. PATENT DOCUMENTS 7,373,775 B2 5/2008 Breuer et al.
7,707,824 B2 5/2010 Solbrig
(Continued)

FOREIGN PATENT DOCUMENTS

CN 103046990 A 4/2013
JP 2014-169912 A 9/2014

OTHER PUBLICATIONS

First Office Action issued for Chinese Patent Application No. CN 201980062139.X dated Feb. 25, 2022, 7 pages.
(Continued)

*Primary Examiner* — Brandon D Lee
(74) *Attorney, Agent, or Firm* — Foley & Lardner LLP

(57) ABSTRACT

An aftertreatment system configured to reduce constituents of an exhaust gas produced by an engine comprises an aftertreatment component and an optical assembly. The optical assembly comprises an optical emitter configured to emit light onto a face of the aftertreatment component, and an optical detector configured to detect light reflected from the face of the aftertreatment component. A controller is configured to determine at least one of an amount of NOx gases or an amount of ammonia on the face of the aftertreatment component based on an optical parameter of the detected light that has reflected from the face of the aftertreatment component.

13 Claims, 8 Drawing Sheets

Related U.S. Application Data

(60) Provisional application No. 62/734,460, filed on Sep. 21, 2018.

(51) Int. Cl.
| | | |
|---|---|---|
| *F01N 11/00* | (2006.01) | |
| *G01N 21/33* | (2006.01) | |
| *G01N 21/3504* | (2014.01) | |
| *G01N 33/00* | (2006.01) | |
| *F01N 3/10* | (2006.01) | |

(52) U.S. Cl.
CPC ..... *G01N 21/3504* (2013.01); *G01N 33/0037* (2013.01); *F01N 3/106* (2013.01); *F01N 2560/021* (2013.01); *F01N 2560/026* (2013.01); *F01N 2610/02* (2013.01); *F01N 2610/14* (2013.01); *F01N 2900/1614* (2013.01); *F01N 2900/1622* (2013.01)

(58) Field of Classification Search
CPC ........... F01N 2560/026; F01N 2610/02; F01N 2610/14; F01N 2900/1614; F01N 2900/1622; F01N 2560/12; G01N 21/33; G01N 21/3504; G01N 33/0037; Y02T 10/12; Y02T 10/40
See application file for complete search history.

(56) References Cited

U.S. PATENT DOCUMENTS

| | | |
|---|---|---|
| 8,208,143 B2 | 6/2012 | Goto et al. |
| 8,733,083 B2 | 5/2014 | Ofoli et al. |
| 9,038,373 B2 | 5/2015 | Geveci et al. |
| 2009/0039284 A1 | 2/2009 | Goto et al. |
| 2010/0242454 A1 | 9/2010 | Holderbaum |
| 2011/0154806 A1 | 6/2011 | Hoyte et al. |
| 2011/0299076 A1 | 12/2011 | Feitisch et al. |
| 2014/0075590 A1 | 1/2014 | Janssen et al. |
| 2014/0183380 A1 | 7/2014 | Ukon et al. |
| 2015/0013309 A1 | 1/2015 | Upadhyay et al. |
| 2016/0333760 A1* | 11/2016 | Blomgren ............... F01N 3/208 |
| 2017/0370262 A1 | 12/2017 | Zoran et al. |
| 2018/0266293 A1 | 9/2018 | Moon et al. |

OTHER PUBLICATIONS

International Search Report and Written Opinion issued for PCT Application No. PCT/US2019/045931 dated Oct. 29, 2019.

\* cited by examiner

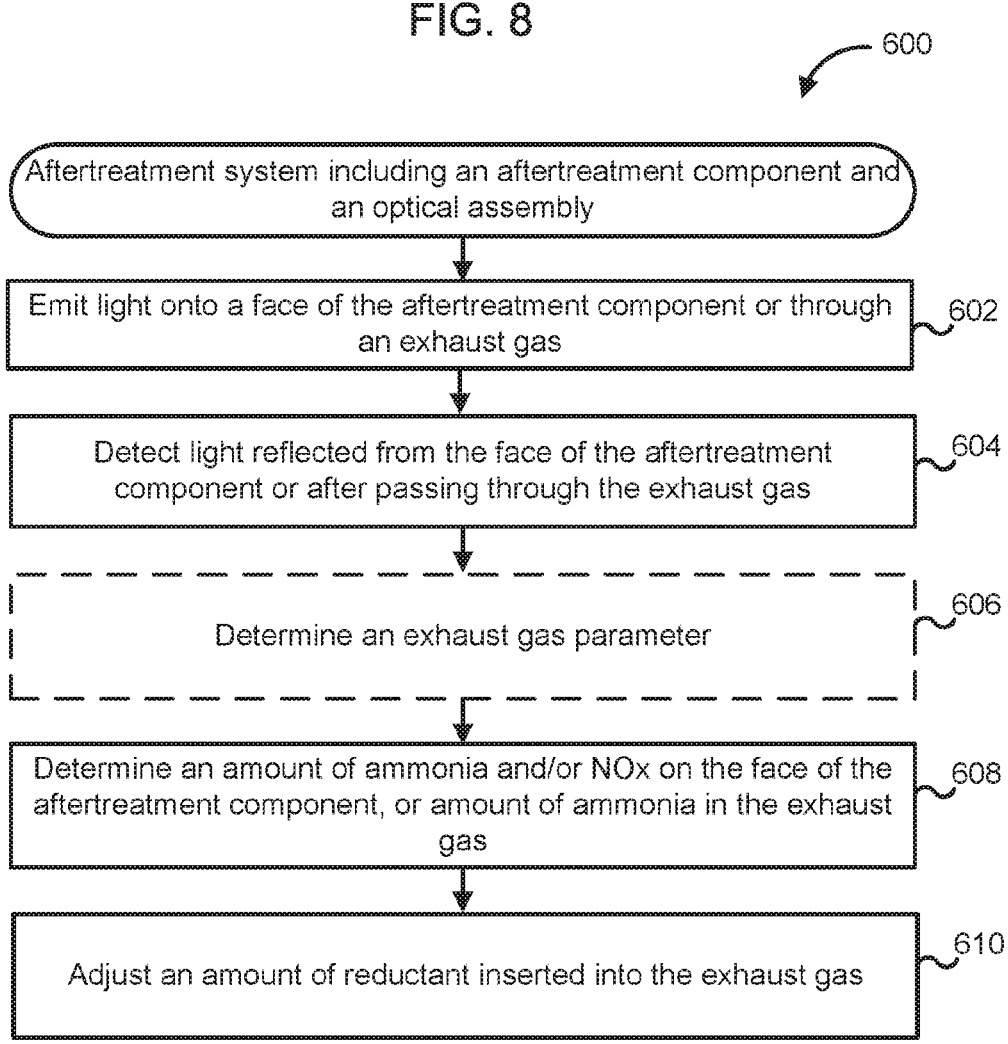

OPTICAL SENSING OF $NO_x$ AND AMMONIA IN AFTERTREATMENT SYSTEMS

CROSS REFERENCE TO RELATED APPLICATIONS

The present application is a divisional of U.S. patent application Ser. No. 17/277,900, filed Mar. 19, 2021, which is a national stage of PCT Application No. PCT/US2019/045931, filed Aug. 9, 2019, which claims the benefit of U.S. Provisional Patent Application No. 62/734,460, filed Sep. 21, 2018. The contents of these applications are incorporated herein by reference in their entireties.

TECHNICAL FIELD

The present disclosure relates generally to aftertreatment systems for use with internal combustion (IC) engines.

BACKGROUND

Exhaust aftertreatment systems are used to receive and treat exhaust gas generated by IC engines. Generally, exhaust gas aftertreatment systems include any of several different components to reduce the levels of harmful exhaust emissions present in the exhaust gas. For example, certain exhaust gas aftertreatment systems for diesel-powered IC engines include a selective catalytic reduction (SCR) system including a catalyst formulated to convert $NO_x$ (NO and $NO_2$ in some fraction) into harmless nitrogen gas ($N_2$) and water vapor ($H_2O$) in the presence of ammonia ($NH_3$). Generally in such aftertreatment systems, an exhaust reductant (e.g., a diesel exhaust fluid such as a urea solution) is injected into the SCR system to provide a source of ammonia, and mixed with the exhaust gas to partially reduce the $NO_x$ gases. The reduction byproducts of the exhaust gas are then fluidly communicated to the catalyst included in the SCR system to decompose substantially all of the $NO_x$ gases into relatively harmless byproducts which are expelled out of the aftertreatment system.

Measuring an amount of $NO_x$ gases and/or ammonia in the exhaust gas is desirable for efficient insertion of reductant in aftertreatment systems. The amount of ammonia in the exhaust gas can indicate how efficiently the reductant is decomposing in the exhaust gas, an ammonia capacity, or catalytic conversion efficiency of a SCR catalyst or an ammonia oxidation ($AMO_x$) catalyst, respectively if the ammonia concentration is measured downstream of the catalyst. Similarly, measuring concentration of ammonia or $NO_x$ adsorbed on a face of the SCR catalyst or $AMO_x$ catalyst can indicate an ammonia absorbing capacity or catalytic conversion efficiency, respectively, of the SCR catalyst, or indicate a catalytic conversion efficiency of the $AMO_x$ catalyst. These parameters can be used to control the amount of reductant inserted into the aftertreatment system for reducing reductant consumption, increasing catalytic conversion efficiency, reducing ammonia slip and/or included in system diagnostics to detect any abnormalities in operation of the aftertreatment system.

SUMMARY

Embodiments described herein relate generally to systems and methods for optically sensing an amount of ammonia and/or $NO_x$ on a face of an aftertreatment component, and/or in exhaust gas flowing through an aftertreatment system. In particular, systems and methods described herein comprise diffuse or specular optical assemblies configured to measure an amount of NO or ammonia on a face of a catalyst, or an amount of ammonia in the exhaust gas flowing through the aftertreatment system.

In one embodiment, an aftertreatment system configured to reduce constituents of an exhaust gas produced by an engine comprises an aftertreatment component, and an optical assembly. The optical assembly comprises an optical emitter configured to emit light onto a face of the aftertreatment component, and an optical detector configured to detect light reflected from the face of the aftertreatment component. A controller is configured to determine at least one of an amount of $NO_x$ gases or an amount of ammonia on the face of the aftertreatment component based on an optical parameter of the detected light that has reflected from the face of the aftertreatment component.

In another embodiment, an aftertreatment system configured to reduce constituents of an exhaust gas produced by an engine comprises an aftertreatment component, and an optical assembly. The optical assembly comprises an optical emitter configured to emit light through the exhaust gas, and an optical detector configured to detect light that has passed through the exhaust gas. A controller is configured to determine an amount of ammonia in the exhaust gas based on an optical parameter of the detected light that has passed through the exhaust gas.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The foregoing and other features will become more fully apparent from the following description and appended claims, taken in conjunction with the accompanying drawings. Embodiments of the invention will be described with additional specificity and detail through use of the accompanying drawings. However, the drawings depict only examples and are not to be considered limiting of the scope of the invention.

FIG. 8 is a schematic flow diagram of a method for controlling an amount of reductant inserted into an aftertreatment system based on an amount of ammonia in an exhaust gas flowing through the aftertreatment system or an amount of $NO_x$ gases or ammonia adsorbed on a face of an aftertreatment component of the aftertreatment system, according to an embodiment.

Figure 1:
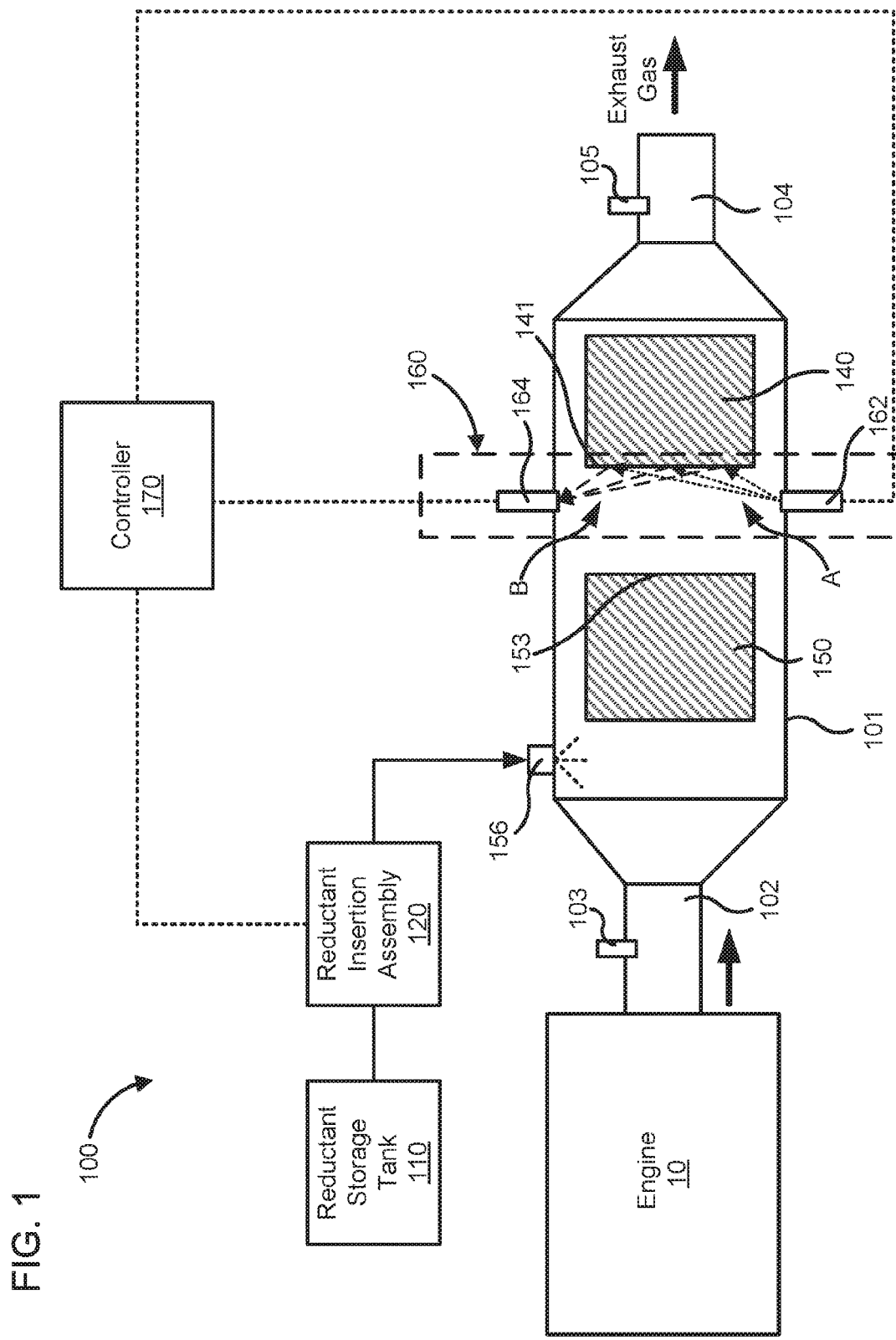
FIG. 1 is a schematic illustration of an aftertreatment system, according to an embodiment.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Embodiments described herein relate generally to systems and methods for optically sensing an amount of ammonia and/or $NO_x$ on a face of an aftertreatment component, and/or in exhaust gas flowing through an aftertreatment system. In particular, systems and methods described herein comprise diffuse or specular optical assemblies configured to measure an amount of $NO_x$ or ammonia on a face of a catalyst, or an amount of ammonia in the exhaust gas flowing through the aftertreatment system.

Measurement of $NO_x$ or ammonia adsorbed in SCR catalysts, which may correlate to catalytic conversion efficiency or ammonia storage capacity, respectively, of the SCR catalyst, is generally performed indirectly using complex algorithms. Some techniques include estimating $NO_x$ absorption or ammonia capacity of the SCR catalyst via determination of an amount of reductant inserted into the aftertreatment, an amount of $NO_x$ gases in the exhaust gas flowing through the SCR catalyst, and/or an age of a catalyst. Similarly, an amount of ammonia in the exhaust gas is measured indirectly based on the amount of inserted reductant to the exhaust gas, and an amount of $NO_x$ in the exhaust gas. These indirect measurements are prone to errors and increase the complexity of measurement systems. For example, for low temperature applications, the temperature of the aftertreatment system may not get high enough to remove all ammonia from the SCR catalyst and reset a measurement algorithm every 100 hours during a timer based regeneration. Some conventional systems use ammonia sensors for measuring ammonia concentration in the exhaust gas. Such ammonia sensors are, however cross-sensitive to NON, add significant cost to the aftertreatment system, and only function reliably after a start-up period.

Various embodiments of systems and methods described herein for sensing an amount of $NO_x$ and/or ammonia on a face of an aftertreatment component, or an amount of ammonia in an exhaust gas may provide one or more benefits including, for example: (1) providing sensitive measurement of ammonia and/or $NO_x$ coverage on an aftertreatment component such as an SCR or $AMO_x$ catalyst, or an amount of ammonia in an exhaust gas via optical sensors; (2) allowing measurement of ammonia and/or $NO_x$ coverage at an inlet and/or outlet of an aftertreatment component; (3) reducing the amount of reductant consumed while increasing catalytic conversion efficiency by adjusting an amount of reductant inserted into the aftertreatment system based on accurate measurements of ammonia and/or $NO_x$ coverage of an aftertreatment component, and/or an amount of ammonia in exhaust gas; and (4) allowing use of the parameters in an onboard diagnostic systems to detect any abnormalities in operation of the aftertreatment system.

FIG. 1 is a schematic illustration of an aftertreatment system 100, according to an embodiment. The aftertreatment system 100 is coupled to an engine 10 (e.g., a diesel engine, a gasoline engine, a natural gas engine, a biodiesel engine, a dual fuel engine, an alcohol engine, an E85 or any other suitable internal combustion engine) and configured to receive an exhaust gas (e.g., a diesel exhaust gas) therefrom. The aftertreatment system 100 is configured to reduce constituents of the exhaust gas such as, for example, $NO_x$ gases (e.g., NO, $NO_2$, $N_2O$, $NO_3$, etc.), CO, etc. The aftertreatment system 100 may include a reductant storage tank 110, a reductant insertion assembly 120, an aftertreatment component 140, an upstream aftertreatment component 150, an optical assembly 160 and a controller 170.

The aftertreatment system 100 includes a housing 101 defining an internal volume. The housing 101 may be formed from a rigid, heat-resistant and corrosion-resistant material, for example stainless steel, iron, aluminum, metals, ceramics, or any other suitable material. The housing 101 may have any suitable cross-section, for example circular, square, rectangular, oval, elliptical, polygonal, or any other suitable shape.

The aftertreatment component 140 is positioned in the internal volume defined by the housing 101. In some embodiments, the aftertreatment component 140 may include a SCR catalyst formulated to selectively decompose constituents of the exhaust gas. Any suitable catalyst can be used such as, for example, rhodium, cerium, iron, manganese, copper, vanadium based catalyst, any other suitable catalyst, or a combination thereof. The SCR catalyst can be disposed on a suitable substrate such as, for example, a ceramic (e.g., cordierite) or metallic (e.g., kanthal) monolith core which can, for example, define a honeycomb structure. A washcoat can also be used as a carrier material for the SCR catalyst. Such washcoat materials may comprise, for example, aluminum oxide, titanium dioxide, silicon dioxide, any other suitable washcoat material, or a combination thereof. The exhaust gas (e.g., diesel exhaust gas) can flow over and/or around the SCR catalyst such that any NO gases included in the exhaust gas are further reduced to yield an exhaust gas which is substantially free of NO gases.

In some embodiments, the aftertreatment component 140 may include a selective catalytic reduction filter (SCRF) system, or any other aftertreatment component configured to decompose constituents of the exhaust gas (e.g., NO gases such as such nitrous oxide, nitric oxide, nitrogen dioxide, etc.), flowing through the aftertreatment system 100 in the presence of a reductant, as described herein.

In some embodiments, an upstream aftertreatment component 150 may be positioned upstream of the aftertreatment component 140 within the internal volume of the housing 101. In some embodiments, the upstream aftertreatment component 150 may include an SCR catalyst. In such embodiments, the aftertreatment component 140 may also include a SCR catalyst, an AMOK catalyst (e.g., to decompose any unreacted ammonia in the exhaust gas so as to reduce ammonia slip) or a combination thereof.

In some embodiments, a plurality of aftertreatment components may be positioned within the internal volume defined by the housing 101 in addition to the aftertreatment component 140 and the upstream aftertreatment component 150. Such aftertreatment components may include, for example, filters (e.g., particulate matter filters, catalyzed filters, etc.), oxidation catalysts (e.g., carbon monoxide and/or hydrocarbons catalysts), mixers, baffle plates, or any other suitable aftertreatment component.

An inlet conduit 102 is coupled to an inlet of the housing 101 and structured to receive exhaust gas from the engine 10 and communicate the exhaust gas to an internal volume defined by the housing 101. Furthermore, an outlet conduit 104 may be coupled to an outlet of the housing 101 and structured to expel treated exhaust gas into the environment. A first sensor 103 may be positioned in the inlet conduit 102. The first sensor 103 may comprise a $NO_x$ sensor configured to measure an amount of NO gases included in the exhaust gas and may include a physical NO sensor or a virtual NO sensor. In other embodiments, the first sensor 103 may include a temperature sensor, a pressure sensor, an oxygen sensor or any other sensor configured to measure one or more exhaust gas parameters (e.g., temperature, pressure, flow rate, amount of NO in exhaust gas, etc.).

A second sensor 105 may be positioned in the outlet conduit 104. The second sensor 105 may comprise a second NO sensor configured to determine an amount of NO gases in the exhaust gas expelled into the environment after passing through the aftertreatment component 140 (e.g., an SCR catalyst and/or an AMOK catalyst). In other embodiments, the second sensor 105 may include a particulate matter sensor.

A reductant port 156 may be positioned on the housing 101 and structured to allow insertion of a reductant into a flow path of the exhaust gas flowing through the aftertreatment system 100. As shown in FIG. 1, the reductant port 156 is positioned upstream of the upstream aftertreatment component 150 on the housing 101. In other embodiments, the reductant port 156 may be provided on the inlet conduit 102. In still other embodiments, the reductant port 156 may be positioned over the aftertreatment component 140 or the upstream aftertreatment component 150 to deliver the reductant directly onto the aftertreatment component 140 or the upstream aftertreatment component 150, respectively.

The reductant storage tank 110 is structured to store the reductant. The reductant is formulated to facilitate decomposition of the constituents of the exhaust gas (e.g., $NO_x$ gases included in the exhaust gas). Any suitable reductant can be used. In some embodiments, the exhaust gas comprises a diesel exhaust gas and the reductant comprises a diesel exhaust fluid. For example, the diesel exhaust fluid may comprise urea, an aqueous solution of urea, or any other fluid that comprises ammonia, by-products, or any other diesel exhaust fluid as is known in the arts (e.g., the diesel exhaust fluid marketed under the name ADBLUE®). In particular embodiments, the reductant comprises an aqueous urea solution having a particular ratio of urea to water. For example, the reductant may comprise an aqueous urea solution including 32.5% by volume of urea and 67.5% by volume of deionized water, or 40% by volume of urea and 60% by volume of deionized water.

A reductant insertion assembly 120 is fluidly coupled to the reductant storage tank 110. The reductant insertion assembly 120 is configured to selectively insert the reductant into the exhaust gas flow path through the reductant port 156. The reductant insertion assembly 120 may include a pump configured to pump a predetermined amount of reductant into the flow path of the exhaust gas. The pump may be, for example, a centrifugal pump, a suction pump, a positive displacement pump, a diaphragm pump or any other suitable pump.

Screens, check valves, pulsation dampers, or other structures may also be positioned downstream of the pump to provide the reductant to the exhaust gas. In various embodiments, the reductant insertion assembly 120 may also comprise a blending chamber structured to receive pressurized reductant from a metering valve positioned downstream of the pump at a controllable rate. The blending chamber may also be structured to receive air, or any other inert gas (e.g., nitrogen), for example, from an air supply unit so as to deliver a combined flow of the air and the reductant into the exhaust gas through the reductant port 156. In various embodiments, a nozzle may be provided in the reductant port 156 and structured to deliver a stream or a jet of the reductant into the internal volume of the housing 101 so as to deliver the reductant into the exhaust gas.

In various embodiments, the reductant insertion assembly 120 may also comprise a dosing valve for selectively delivering the reductant from the reductant insertion assembly 120 into the exhaust gas flow path. The dosing valve can comprise any suitable valve, for example a butterfly valve, a gate valve, a check valve (e.g., a tilting disc check valve, a swing check valve, an axial check valve, etc.), a ball valve, a spring loaded valve, an air assisted injector, a solenoid valve, or any other suitable valve.

The aftertreatment system 100 also includes an optical assembly 160. The optical assembly 160 includes an optical emitter 162 configured to emit light A onto a face of the aftertreatment component 140, and an optical detector 164 configured to detect light reflected B from the face of the aftertreatment component 140. For example, as shown in FIG. 1, the optical emitter 162 is coupled to the housing 101 at a first location, for example, disposed through a wall of the housing 101 at the first location that is between the aftertreatment component 140 and the upstream aftertreatment component 150. The optical emitter 162 may include a diffuse light source, for example, a light emitting diode (LED). In some embodiments, the emitted light may have a wavelength in the infrared (IR) range. In other embodiments, the emitted light may have a wavelength in the ultraviolet-visible (UV-vis) range.

The optical emitter is 162 is configured to emit light A onto any suitable location on the inlet face 141 of the aftertreatment component 140, for example, any radial position of the inlet face 141 and/or a midpoint location of the inlet face 141 of the aftertreatment component 140. Furthermore, the optical detector 164 is coupled to a second location of the housing 101, for example, disposed through the wall of the housing 101 at the second location. The second location may be opposite the first location or may include any other suitable location of the housing 101. The optical detector 164 may be a photodiode, a pyroelectric detector, a photon detector, a photomultiplier tube or any other suitable optical detector.

The optical detector 164 is configured to detect light B reflected from the inlet face 141 of the aftertreatment component 140. The light is reflected diffusely. In other words, the optical assembly 160 is operated on the principles of diffused reflectance. An optical parameter (e.g., an intensity, a frequency, a wavelength, etc.) of the light B reflected from the inlet face 141 of the aftertreatment component 140 corresponds to an amount of $NO_x$ gases or an amount of ammonia on the face of the aftertreatment component 140. For example, the ammonia and/or $NO_x$ adsorbed on the inlet face 141 may absorb a portion of the emitted light A causing the reflected light B to have a lower intensity than the emitted light A, such that an absorbance (i.e., difference between intensity of the emitted and reflected light) corresponds to an amount of ammonia and/or NO gases present on the inlet face 141.

Expanding further, the ammonia and NO adsorbed on the inlet face 141 of the aftertreatment component 140 may preferentially absorb light in the specific wavelength of the emitted light (e.g., particular IR wavelengths or particular UV-vis wavelengths), relative to other molecules adsorbed on the inlet face 141 (e.g., $H_2O$, $CO_2$, hydrocarbons, etc.) or materials forming the aftertreatment component 141 (e.g., catalyst materials, washcoat materials or binder materials). Thus, absorbance peaks detected by the optical detector correspond to ammonia and/or NO adsorbed on the inlet face 141. In this manner, the optical assembly 160 may selectively detect amount of ammonia and/or NO adsorbed on the inlet face.

In some embodiments in which the aftertreatment component 140 includes a SCR catalyst, the amount of ammonia on the inlet face 141 may correspond to an ammonia storage level of the aftertreatment component 140 (i.e., an amount of ammonia stored in SCR catalyst). In other embodiments, the amount of NO gases adsorbed on the inlet face 141 may correspond to a catalytic conversion efficiency of the aftertreatment component 140. In still other embodiments, the aftertreatment component 140 may include an AMOK catalyst. In such embodiments, the optical parameter of the detected light may correspond to an amount of ammonia adsorbed on the inlet face 141 of the aftertreatment component 140, which may correspond to a catalytic conversion efficiency of the aftertreatment component 140.

The aftertreatment system 100 also includes the controller 170 operatively coupled to the optical assembly 160. For example, the controller 170 is communicatively coupled to the optical emitter 162 and configured to send an activation signal to the optical emitter 162 causing the optical emitter 162 to emit light. The controller 170 may activate the optical emitter 162 at any suitable frequency, for example, every 1 second, 5 seconds, 10 seconds, 30 seconds, 1 minute, 2 minutes, 5 minutes or 10 minutes, inclusive of all ranges and values therebetween. In other embodiments, the controller 170 may be configured to activate (e.g., turn ON) the optical emitter 162 when the aftertreatment system 100 is activated, for example, when the engine 10 is turned ON, and deactivate (e.g., turn OFF) the optical emitter 162 when the aftertreatment system 100 is deactivated, for example, when the engine 10 is turned OFF. In other words, the optical emitter 162 continuously emits light when the engine 10 is turned ON and the aftertreatment system 100 is active, so as to provide real time measurement of ammonia and/or NON.

The controller 170 is also communicatively coupled to the optical detector 164 and configured to receive a detector signal therefrom. The detector signal may include an electrical signal (e.g., a current or voltage) generated by the optical detector 164, which corresponds to an optical parameter (e.g., intensity) of the detected light that has reflected from the inlet face 141 of the aftertreatment component 140. The controller 170 is configured to determine an amount of ammonia and/or $NO_x$ gases adsorbed on the inlet face 141 of the aftertreatment component 140 based on the optical parameter. For example, the controller 170 may be configured to determine the amount of $NO_x$ and/or ammonia gases (or otherwise any chemical species) on the inlet face 141 of the aftertreatment component 140 based on a difference between a parameter of the light emitted from the optical emitter 162 (e.g., a first intensity) and a parameter of the detected light that has reflected from the inlet face 141 of the aftertreatment component 140. For example, the difference may be equal to an absorbance of the light by the $NO_x$ and/or ammonia on the inlet face 141, and correspond to the amount of the $NO_x$ and/or ammonia adsorbed thereon.

While the optical assembly 160 or any other sensing assembly described herein are described as configured to detect ammonia and/or $NO_x$ gases adsorbed on the inlet face 141 of the aftertreatment component 140 (e.g., a SCR catalyst), in other embodiments, the optical assembly 160 or any other optical assembly described herein may be configured to measure an amount of any other molecule adsorbed on the inlet face 141 of the aftertreatment component 140, any other face of the aftertreatment component 140 or the upstream aftertreatment component 150. Such molecules may include, for example, CO, $CO_2$, $SO_x$ gases, etc.

In some embodiments, the controller 170 may include algorithms or lookup tables configured to determine an amount of $NO_x$ and/or ammonia adsorbed over the entire volume of the aftertreatment component 140 based on the amount of $NO_x$ and/or ammonia on the inlet face 141. For example, the controller 170 may be configured to determine an ammonia storage level of the aftertreatment component 140. In other embodiments, the controller 170 may also include algorithms, equations or lookup tables to calibrate the optical assembly 160 to account for variations in exhaust gas parameters, for example, variations in exhaust temperatures, pressure or flow rate (e.g., determined based on engine speed and/or torque), and/or amount of water in the exhaust gas. The exhaust gas parameters may be determined from exhaust gas parameter signals received from the engine 10, the first sensor 103 and/or the second sensor 105, or a virtual sensor.

The emitted light may have a wavelength in the infrared (IR) range. IR light is sensitive to temperature, so the controller 170 may be configured to calibrate the optical parameter value determined from the detector signal based on one or more exhaust gas parameters, for example, the exhaust gas temperature (e.g., determined by the first sensor 103), an exhaust gas flow rate (e.g., determined from the engine speed and/or torque), an exhaust gas pressure and/or an amount of water in exhaust gas (e.g., determined by the first sensor 103), and accurately determine an amount of $NO_x$ gases or ammonia on the inlet face 141 of the aftertreatment component 140. In still another embodiment, the controller 170 may include signal filters (e.g., low pass filters, high pass filters, band pass filters, etc.) or any other suitable signal filters to filter noise from the detector signal.

In some embodiment, the controller 170 may also be communicatively coupled to the reductant insertion assembly 120. The controller 170 may be configured to activate the reductant insertion assembly 120 based on the amount of $NO_x$ gases and/or ammonia on the inlet face 141 of the aftertreatment component 140. In this manner, the controller 170 may reduce reductant consumption, increase catalytic conversion efficiency of the aftertreatment component 140 (e.g., an SCR catalyst or an AMOK catalyst) and/or reduce ammonia slip.

The controller 170 may be operatively coupled to optical assembly 160 and/or the reductant insertion assembly 120 using any type and any number of wired or wireless connections. For example, a wired connection may include a serial cable, a fiber optic cable, a CAT5 cable, or any other form of wired connection. Wireless connections may include the Internet, Wi-Fi, cellular, radio, Bluetooth, ZigBee, etc. In one embodiment, a controller area network (CAN) bus provides the exchange of signals, information, and/or data. The CAN bus includes any number of wired and wireless connections.

Figure 2:
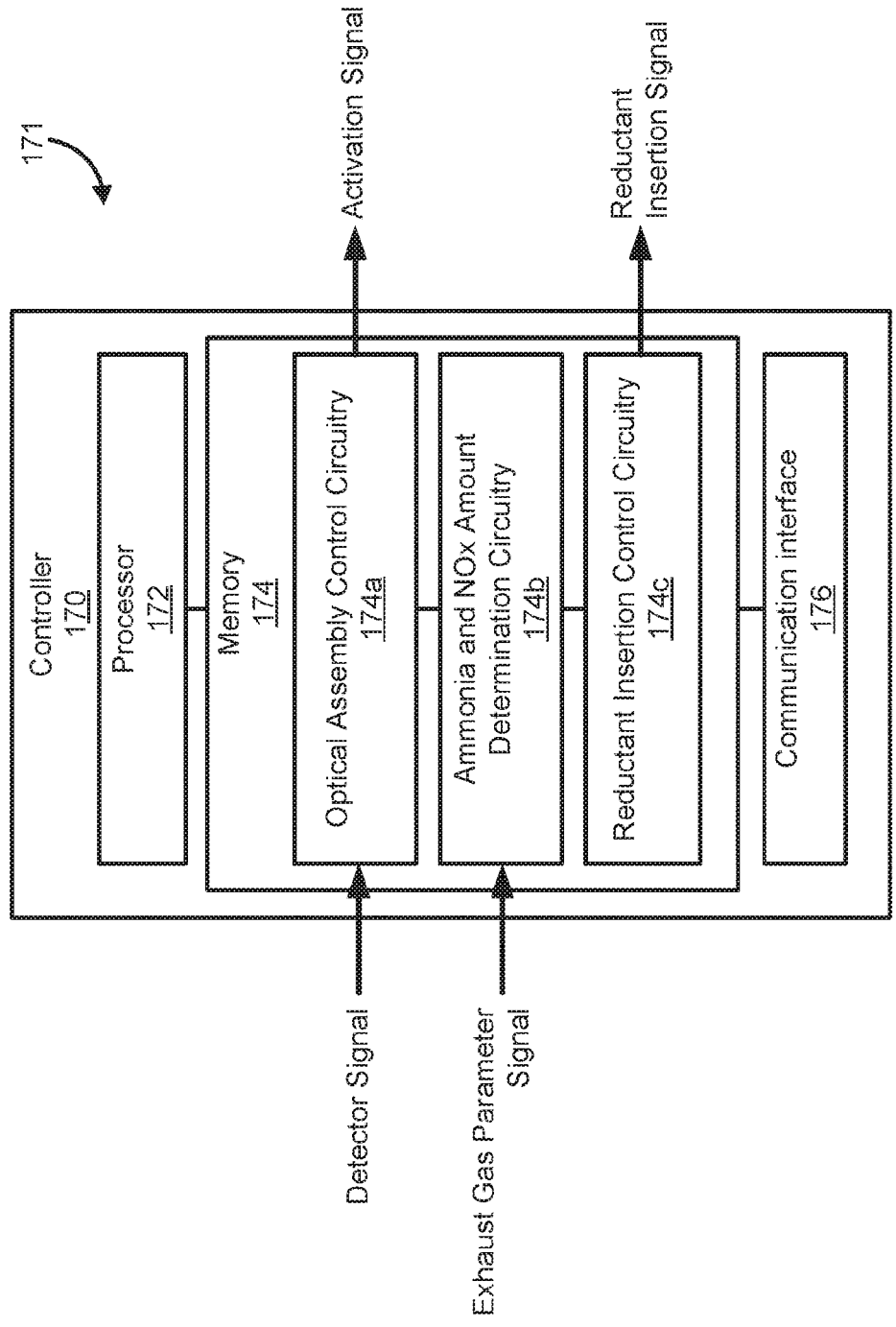
FIG. 2 is schematic block diagram of a control circuitry that can include a controller of the aftertreatment system of FIG. 1, according to an embodiment.

In particular embodiments, the controller 170 can be included in a control circuitry. For example, FIG. 2 is a schematic block diagram of a control circuitry 171 that comprises the controller 170, according to an embodiment. The controller 170 comprises a processor 172, a memory 174, or any other computer readable medium, and a communication interface 176. Furthermore, the controller 170 includes an optical assembly control circuitry 174a, an ammonia and $NO_x$ amount determination circuitry 174b and a reductant insertion control circuitry 174c. It should be understood that the controller 170 shows only one embodiment of the controller 170 and any other controller capable of performing the operations described herein can be used.

The processor 172 can comprise a microprocessor, programmable logic controller (PLC) chip, an ASIC chip, or any other suitable processor. The processor 172 is in communication with the memory 174 and configured to execute instructions, algorithms, commands, or otherwise programs stored in the memory 174.

The memory 174 comprises any of the memory and/or storage components discussed herein. For example, memory 174 may comprise a RAM and/or cache of processor 172. The memory 174 may also comprise one or more storage devices (e.g., hard drives, flash drives, computer readable media, etc.) either local or remote to controller 170. The memory 174 is configured to store look up tables, algorithms, or instructions.

In one configuration, the optical assembly control circuitry 174a, the ammonia and $NO_x$ amount determination circuitry 174b and the reductant insertion control circuitry 174c are embodied as machine or computer-readable media (e.g., stored in the memory 174) that is executable by a processor, such as the processor 172. As described herein and amongst other uses, the machine-readable media (e.g., the memory 174) facilitates performance of certain operations to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). Thus, the computer readable media may include code, which may be written in any programming language including, but not limited to, Java or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus, etc.).

In another configuration, the optical assembly control circuitry 174a, the ammonia and $NO_x$ amount determination circuitry 174b and the reductant insertion control circuitry 174c are embodied as hardware units, such as electronic control units. As such, the optical assembly control circuitry 174a, the ammonia and $NO_x$ amount determination circuitry 174b and the reductant insertion control circuitry 174c may be embodied as one or more circuitry components including, but not limited to, processing circuitry, network interfaces, peripheral devices, input devices, output devices, sensors, etc.

In some embodiments, the optical assembly control circuitry 174a, the ammonia and $NO_x$ amount determination circuitry 174b and the reductant insertion control circuitry 174c may take the form of one or more analog circuits, electronic circuits (e.g., integrated circuits (IC), discrete circuits, system on a chip (SOCs) circuits, microcontrollers, etc.), telecommunication circuits, hybrid circuits, and any other type of "circuit." In this regard, the optical assembly control circuitry 174a, the ammonia and $NO_x$ amount determination circuitry 174b and the reductant insertion control circuitry 174c may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on.

Thus, the optical assembly control circuitry 174a, the ammonia and $NO_x$ amount determination circuitry 174b and the reductant insertion control circuitry 174c may also include programmable hardware devices such as field programmable gate arrays, programmable array logic, programmable logic devices or the like. In this regard, the optical assembly control circuitry 174a, the ammonia and NO amount determination circuitry 174b and the reductant insertion control circuitry 174c may include one or more memory devices for storing instructions that are executable by the processor(s) of the optical assembly control circuitry 174a, the ammonia and $NO_x$ amount determination circuitry 174b and the reductant insertion control circuitry 174c. The one or more memory devices and processor(s) may have the same definition as provided below with respect to the memory 174 and the processor 172.

In the example shown, the controller 170 includes the processor 172 and the memory 174. The processor 172 and the memory 174 may be structured or configured to execute or implement the instructions, commands, and/or control processes described herein with respect to the optical assembly control circuitry 174a, the ammonia and $NO_x$ amount determination circuitry 174b and the reductant insertion control circuitry 174c. Thus, the depicted configuration represents the aforementioned arrangement where the optical assembly control circuitry 174a, the ammonia and NO amount determination circuitry 174b and the reductant insertion control circuitry 174c are embodied as machine or computer-readable media. However, as mentioned above, this illustration is not meant to be limiting as the present disclosure contemplates other embodiments such as the aforementioned embodiment where the optical assembly control circuitry 174a, the ammonia and NO amount determination circuitry 174b and the reductant insertion control circuitry 174c, or at least one circuit of the optical assembly control circuitry 174a, the ammonia and NO amount determination circuitry 174b and the reductant insertion control circuitry 174c are configured as a hardware unit. All such combinations and variations are intended to fall within the scope of the present disclosure.

The processor 172 may be implemented as one or more general-purpose processors, an application specific integrated circuit (ASIC), one or more field programmable gate arrays (FPGAs), a digital signal processor (DSP), a group of processing components, or other suitable electronic processing components. In some embodiments, the one or more processors may be shared by multiple circuits (e.g., the optical assembly control circuitry 174a, the ammonia and NO amount determination circuitry 174b and the reductant insertion control circuitry 174c) may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. All such variations are intended to fall within the scope of the present disclosure. The memory 174 (e.g., RAM, ROM, Flash Memory, hard disk storage, etc.) may store data and/or computer code for facilitating the various processes described herein. The memory 174 may be communicably connected to the processor 172 to provide computer code or instructions to the processor 172 for executing at least some of the processes described herein. Moreover, the memory 174 may be or include tangible, non-transient volatile memory or non-volatile memory. Accordingly, the memory 174 may include database components, object code components, script components, or any other type of information structure for supporting the various activities and information structures described herein.

The communication interface 176 may include wireless interfaces (e.g., jacks, antennas, transmitters, receivers, communication interfaces, wire terminals, etc.) for conducting data communications with various systems, devices, or networks. For example, the communication interface 176 may include an Ethernet card and port for sending and receiving data via an Ethernet-based communications network and/or a Wi-Fi communication interface for communicating with the engine 10, the first sensor 103, the second sensor 105, the optical assembly 160, the reductant insertion assembly 120, or another controller (e.g., an engine control unit). The communication interface 176 may be structured to communicate via local area networks or wide area networks (e.g., the Internet, etc.) and may use a variety of communications protocols (e.g., IP, LON, Bluetooth, ZigBee, radio, cellular, near field communication, etc.).

The optical assembly control circuitry 174a is configured to generate an activation signal configured to activate the optical emitter 162. For example, the optical assembly control circuitry 174a may be configured to continuously activate the optical emitter 162 (e.g., for an entire period during which the aftertreatment system 100 is active) or activate the optical emitter 162 at a predetermined frequency, as previously described herein. The optical assembly control circuitry 174a is also configured to receive a detector signal from the optical detector 164 (e.g., an electrical signal such as a current or a voltage). The detector signal corresponds to the optical parameter of the detected light (e.g., an intensity, frequency, wavelength, time of flight, etc.).

The ammonia and $NO_x$ amount determination circuitry 174b is configured to interpret the detector signal and determine an amount of $NO_x$ and/or ammonia adsorbed on the inlet face 141 of the aftertreatment component 140. For example, the ammonia and $NO_x$ amount determination circuitry 174b may include algorithms or look up tables configured to correlate a value of the optical parameter of the detected light (e.g., an intensity or absorbance) to an amount of ammonia and/or $NO_x$ on the inlet face 141.

In some embodiments, the ammonia and $NO_x$ amount determination circuitry 174b may also be configured to receive one or more exhaust gas parameter signals, for example, from the engine 10, the first sensor 103 and/or the second sensor 105 and determine one or more exhaust gas parameters (e.g., exhaust gas temperature, flow rate, pressure, amount of $NO_x$ gases in exhaust gas, etc.). The ammonia and $NO_x$ amount determination circuitry 174b may be configured to calibrate or adjust the detector signal based on the one or more exhaust gas parameters, as previously described herein. Furthermore, the ammonia and $NO_x$ amount determination circuitry 174b may also include one or more filters (e.g., low pass filters, high pass filters, band pass filters, etc.) to reduce noise and increase signal to noise ratio.

The reductant insertion control circuitry 174c is configured to generate a reductant insertion signal based on the amount of $NO_x$ gases and/or ammonia gases on a catalyst face 141 or in the exhaust gas. The reductant insertion signal is configured to activate the reductant insertion assembly 120 for inserting a predetermined amount of reductant into the aftertreatment system 100.

For example, in response to the ammonia and $NO_x$ amount determination circuitry 174b determining that an ammonia storage level of the aftertreatment component 140 (e.g., a SCR catalyst) is below a predetermined ammonia storage threshold as determined from the amount of ammonia adsorbed on the inlet face 141, the reductant insertion control circuitry 174c may activate the reductant insertion assembly 120. In other words, in response to the ammonia and $NO_x$ amount determination circuitry 174b determining that an amount of ammonia absorbed over the entire volume of the aftertreatment component 140 (e.g., a SCR catalyst) is below an ammonia storage threshold, the reductant insertion control circuitry 174c of the controller 170 may be configured to instruct the reductant insertion assembly 120 to insert reductant into the exhaust gas. This causes reductant to be inserted into the exhaust gas which decomposes in the exhaust gas to generate ammonia. The ammonia is adsorbed by the aftertreatment component 140 increasing the amount of ammonia stored in the aftertreatment component 140 towards the ammonia storage threshold.

In other embodiments, the ammonia and $NO_x$ amount determination circuitry 174b may determine that an amount of $NO_x$ on the inlet face 141 is above a predetermined $NO_x$ threshold, which may indicate that the aftertreatment component 140 (e.g., a SCR catalyst) is operating at a lower than optimal catalytic conversion efficiency. In such scenarios, the reductant insertion control circuitry 174c may activate the reductant insertion assembly 120, for example, instruct the reductant insertion assembly 120 to insert reductant into the exhaust gas, to increase the amount of ammonia in the exhaust gas so as to increase the catalytic conversion efficiency.

In still other embodiments in which the aftertreatment component 140 includes an $AMO_x$ catalyst, the ammonia and $NO_x$ amount determination circuitry 174b may determine that the amount of ammonia adsorbed in the aftertreatment component 140 is above a predetermined ammonia threshold, which may correspond to aftertreatment component 140 operating at a lower than optimal catalytic conversion efficiency causing ammonia slip downstream of the aftertreatment component 140. In such scenarios, the reductant insertion control circuitry 174c may deactivate the reductant insertion assembly 120 to reduce the amount of ammonia in the exhaust gas so as to reduce ammonia slip downstream of the aftertreatment component 140. In other words, in response to the ammonia and $NO_x$ amount determination circuitry 174b determining that an amount of ammonia absorbed over the entire volume of the aftertreatment component is above the ammonia threshold, the reductant insertion control circuitry 174c may instruct the reductant insertion assembly 120 to stop inserting reductant into the exhaust gas.

While the optical assembly 160 is shown as being configured to measure the amount of ammonia and/or $NO_x$ on the inlet face 141 of the aftertreatment component 140, in other embodiments, the optical emitter 162 may be configured to direct the emitted light A towards an outlet face 153 of the upstream aftertreatment component 150. For example, the upstream aftertreatment component 150 may include a SCR catalyst and the optical assembly 160 may be configured to sense an amount of ammonia and/or $NO_x$ gases on the outlet face 153 of the upstream aftertreatment component 150. The information may be used to determine, for example, an ammonia storage level of the upstream aftertreatment component 150 (e.g., a SCR catalyst), a catalytic conversion efficiency of the upstream aftertreatment component 150 or an ammonia slip through the upstream aftertreatment component 150.

Figure 3:
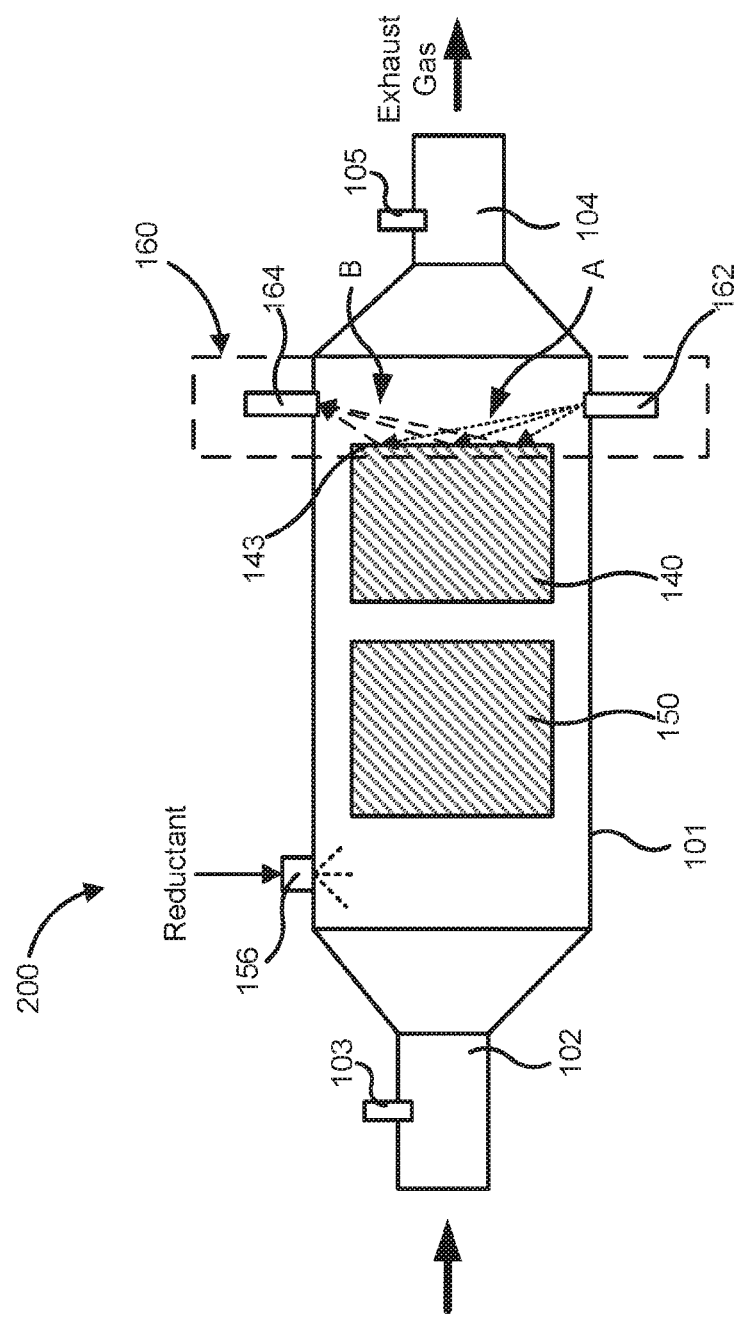
FIG. 3 is a schematic illustration of an aftertreatment system, according to another embodiment

In some embodiments, the optical assembly 160 may be configured to measure an amount of ammonia and/or $NO_x$ on an outlet face 143 of the aftertreatment component 140. For example, FIG. 3 is a schematic illustration of an aftertreatment system 200, according to another embodiment. The aftertreatment system 200 is substantially similar to the aftertreatment system 100 with the following differences. The optical assembly 160 is positioned in the housing 101 downstream of the aftertreatment component 140. The optical emitter 162 is configured to direct emitted light A towards the outlet face 143 of the aftertreatment component 140. The optical detector 164 may be located opposite the optical emitter 162 and detects light B reflected from the outlet face 143 of the aftertreatment component 140. The controller 170 may then be configured to determine an amount of ammonia and/or $NO_x$ gases on the outlet face 143 of the aftertreatment component 140 based on the optical parameter of the reflected light B, as previously described herein. In this manner, the optical assembly 160 may be configured to detect an ammonia storage level of the aftertreatment component 140 (e.g., a SCR catalyst), a catalytic conversion efficiency of the aftertreatment component 140 (e.g., an AMOK catalyst), or an ammonia slip downstream of the aftertreatment component 140.

Figure 4:
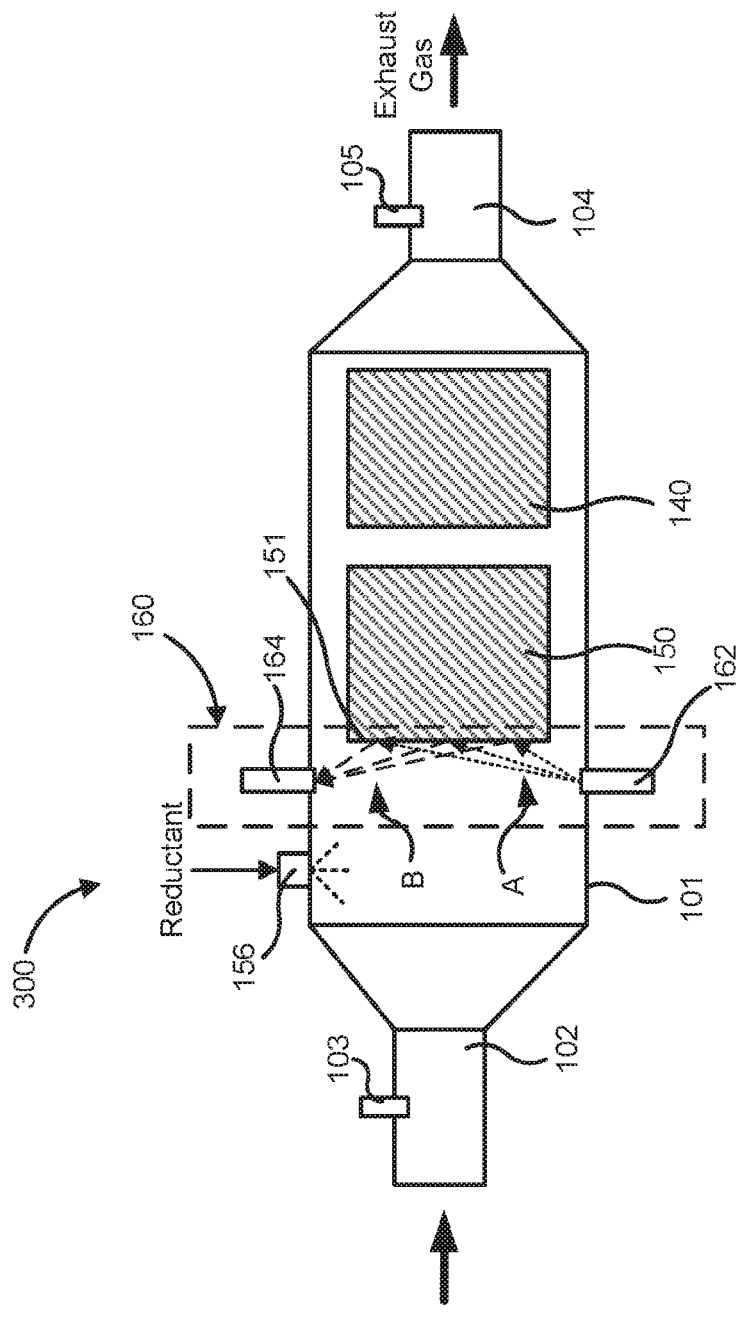
FIG. 4 is a schematic illustration of an aftertreatment system, according to still another embodiment.

In some embodiments, the optical assembly 160 may be configured to measure an amount of ammonia or $NO_x$ gases on an inlet face 151 of the upstream aftertreatment component 150. For example, FIG. 4 is a schematic illustration of an aftertreatment system 300, according to yet another embodiment. The aftertreatment system 300 is substantially similar to the aftertreatment system 100 with the difference that the optical assembly 160 is disposed upstream of the upstream aftertreatment component 150 (e.g., an upstream SCR catalyst). As shown in FIG. 4, the optical emitter 162 is configured to direct the emitted light A onto an inlet face 151 of the upstream aftertreatment component 150. Furthermore, the optical detector 164 is located opposite the optical emitter 162 and configured to detect light B reflected from the inlet face 151 of the upstream aftertreatment component 150. In such embodiments, the controller 170 may be configured to determine an amount of ammonia and/or $NO_x$ on the inlet face 151 of the upstream aftertreatment component 150 based on the optical parameter of the reflected light B and determine, for example, an ammonia storage level or $NO_x$ conversion efficiency of the upstream aftertreatment component 150 therefrom. Furthermore, determining the amount of ammonia on the inlet face 151 of the upstream aftertreatment component 150 may also be used to determine a uniformity index (UI) and/or flow distribution index (FDI) of the reductant in the exhaust gas.

Figure 5:
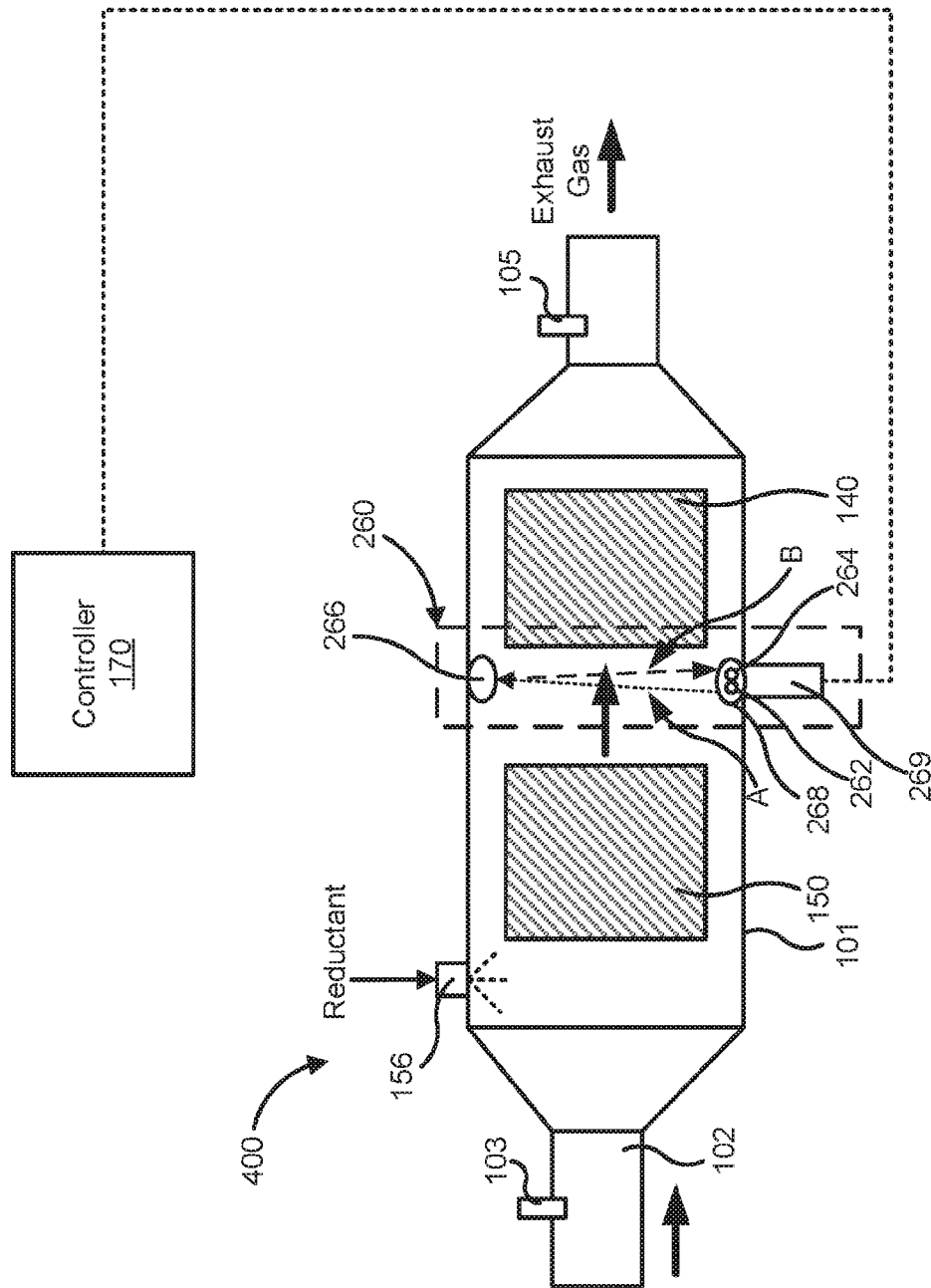
FIG. 5 is a schematic illustration of an aftertreatment system, according to yet another embodiment.

In some embodiments, an aftertreatment system may include an optical assembly configured to detect an amount of ammonia in an exhaust gas flowing through the aftertreatment system. For example, FIG. 5 is a schematic illustration of an aftertreatment system 400, according to an embodiment. The aftertreatment system 400 is substantially similar to the aftertreatment system 100 with the following differences. An optical assembly 260 is positioned between the aftertreatment component 140 and the upstream aftertreatment component 150. The optical assembly 260 includes an optical emitter 262 and an optical detector 264.

The optical emitter 262 is configured to emit light A through the exhaust gas, and the optical detector 264 is configured to detect light B that has passed through the exhaust gas. The controller 170 may be communicatively coupled to the optical emitter 262 and the optical detector 264 (e.g., via electrical couplers included in an optical probe 269 housing the optical emitter 262 an the optical detector 264) and determine an amount of ammonia in the exhaust gas based on an optical parameter of the detected light B that has passed through the exhaust gas, as previously described herein with respect to the optical assembly 160. While described as being configured to detect ammonia, the optical assembly 260 may be configured to detect any constituent of the exhaust gas (e.g., CO, $NO_x$ gases, $SO_x$ gases, etc.).

As shown in FIG. 5, the optical emitter 262 and the optical detector 264 are both located at a first location of the housing 101, for example, disposed adjacent to each other at the first location on a wall of the housing 101. In particular embodiments, the optical emitter 262 and the optical detector 264 may be integrated in the optical probe 269. A first mirror 266 is disposed at a second location of the housing 101 and coupled thereto. The second location may be opposite the first location and in a line of sight of the first location. The first mirror 266 may include a concave mirror configured to reflect light B towards the optical detector 264, which is detected by the optical detector 264. For example, the optical emitter 262 may include a specular light emitter (e.g., an IR laser device, a UV-vis laser device, or a light-emitting diode (LED)). The optical emitter 262 emits light A (e.g., specular light rays) through the exhaust gas towards the first mirror 266. The first mirror 266 reflects the light B that has passed through the exhaust gas towards the optical detector 264, which is then detected by the optical detector 264.

In some embodiments, a second mirror 268 may be positioned at the first location around optical emitter 262 and the optical detector 264. For example, openings may be defined in the second mirror 268 through which the optical emitter 262 and the optical detector 264 may be positioned. In other embodiments, a single opening may be defined in the second mirror 268, for example, at a midpoint of the second mirror 268 (e.g., a concave mirror) and the optical probe 269 housing both the optical emitter 262 and the optical detector 264 may be inserted there. The second mirror 268 reflects at least a portion of the light reflected from the first mirror 266 back towards the first mirror 266. The light may bounce back and forth between the mirrors 266 and 268 before being detected by the optical detector 264. Thus, the effective path length may be substantially greater than a cross-section of the housing 101. For example, the housing 101 may have a cross-section (e.g., a diameter) of 10-20 inches, and the effective path length of the light may be up to 3 meters. Increasing the path length causes the light to pass through the exhaust gas multiple times. This increases the sensitivity of the ammonia measurement, as well as increases the probability of the light reaching the optical detector 264.

In other embodiments, optical detector 264 may be positioned at the second location opposite the first location such that the mirrors 266 and 268 may be excluded. In such embodiments, the emitted light may have sufficient intensity and the optical detector 264 may have sufficient sensitivity to detect change in optical parameter of the exhaust gas after passing only once through the exhaust gas.

Figure 6:
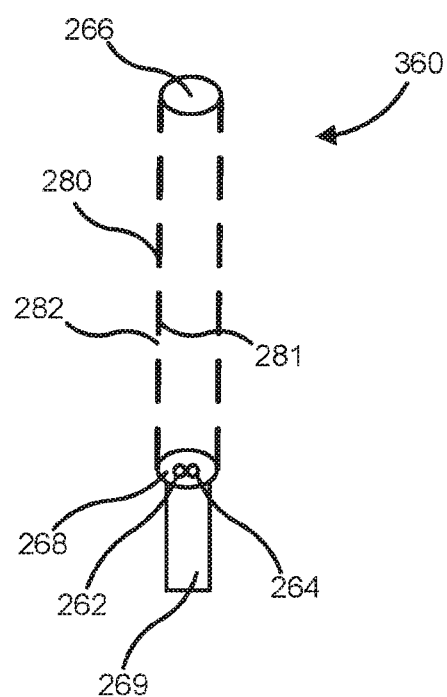
FIG. 6 is a schematic illustration of an optical assembly, according to a particular embodiment.

In some embodiments, an optical assembly may also include a sampling member to sample exhaust gas at various locations of the exhaust gas flow. The emitted light is passed through the sampled portions of the exhaust gas so that a better representation of the amount of ammonia in the exhaust gas may be obtained. For example, FIG. 6 is a schematic illustration of an optical assembly 360. The optical assembly 360 is substantially similar to the optical assembly 260 and includes similar components. In addition, a sampling tube 280 extends from the second mirror 268 to the first mirror 266. The sampling tube 280 may include a hollow tube having a circular cross-section. A plurality of holes 282 are defined through a wall of the sampling tube 280 and are configured to allow a portion of the exhaust gas to pass through the hollow sampling tube 280. The sampling tube 280 may have a length corresponding to a cross-section (e.g., diameter) of the housing 101. The sampling tube 280 may be coupled at its respective axial ends to the mirrors 266 and 268 such that the optical assembly 360 forms an integrated ammonia detection probe insertable into the housing 101 to be positioned within the exhaust gas flow path.

Light emitted by the optical emitter 262 is directed through the hollow sampling tube 280 towards the first mirror 266, and is reflected therefrom towards the optical detector 264, as previously described herein. Furthermore, any light bouncing off the first mirror 266 at an angle away from the optical detector 264 is reflected back towards the optical detector 264 by an inner surface 281 the sampling tube 280. In some embodiments, the inner surface 281 of the sampling tube 280 may be coated with a reflective material (e.g., silver/silver chloride) to facilitate reflection.

FIG. 6 shows the optical assembly 360 as including the cylindrical sampling tube 280. In other embodiments, the optical assembly 360 may include any other sampling structure. For example, in some embodiments, the optical assembly 360 may include an exhaust gas sampling wheel structured to be positioned within the exhaust gas flow path for sampling portions of the exhaust gas. In some embodiments, the exhaust gas sampling wheel may include a circular baffle like structure. In other embodiments, the exhaust gas sampling wheel may include a cross shaped structure having plurality of holes defined through each arm of the cross shaped structure. It should be appreciated that these embodiments are just examples, and in other embodiments, the sampling structure may have any other suitable shape, for example, elliptical, triangular, polygonal, star shaped, etc.

Figure 7:
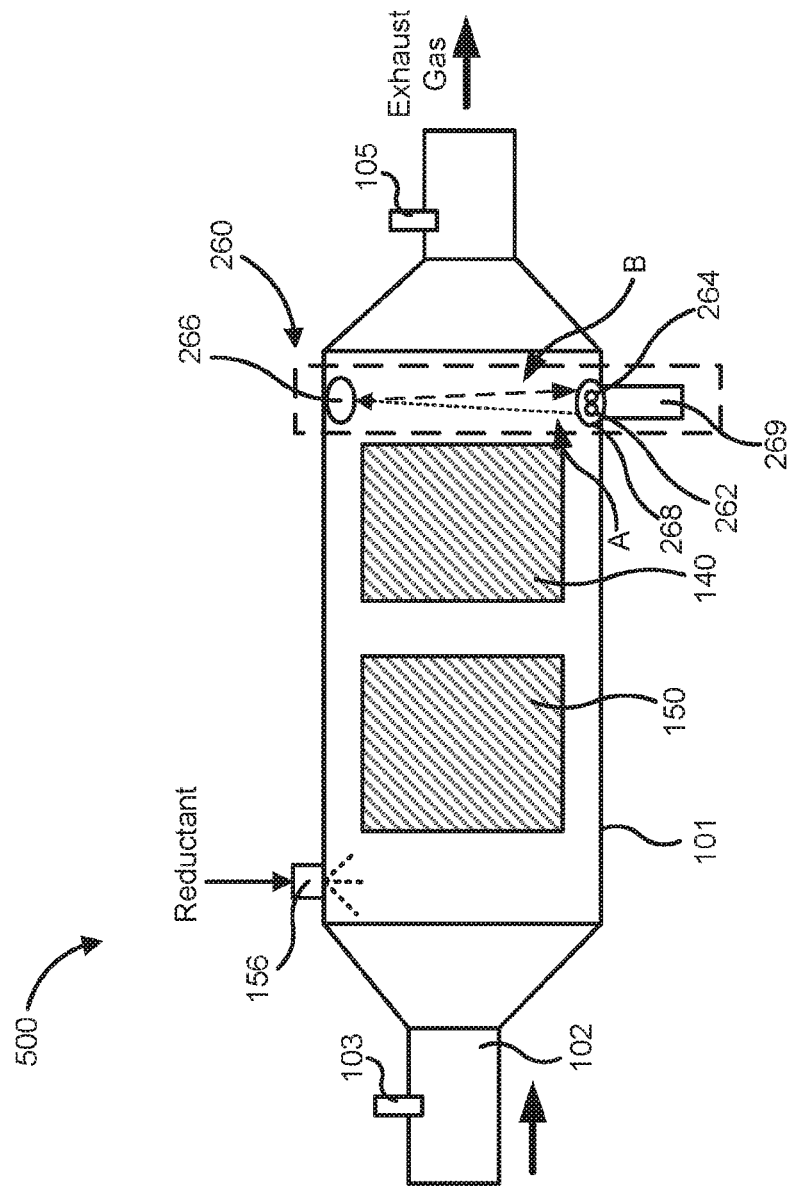
FIG. 7 is a schematic illustration of an aftertreatment system, according to still another embodiment.

In some embodiments, the optical assembly 260 may be positioned in an aftertreatment system so as to measure an amount of ammonia in exhaust gas downstream of an aftertreatment component. For example, FIG. 7 is a schematic illustration of an aftertreatment system 500, according to another embodiment. The aftertreatment system 500 is substantially similar to the aftertreatment system 400, except that the optical assembly 260 is positioned downstream of the aftertreatment component 140. The optical assembly 260 therefore measures an amount of ammonia in the exhaust gas downstream of the aftertreatment component 140 which may correspond to an ammonia slip of the aftertreatment component 140 (e.g., in embodiments in which the aftertreatment component 140 includes a SCR catalyst) or a catalytic conversion efficiency of the aftertreatment component 140 (e.g., in embodiments in which the aftertreatment component 140 includes an $AMO_x$ catalyst).

FIG. 8 is a schematic flow diagram of an example method 600 for determining an amount of $NO_x$ and/or ammonia on a face of an aftertreatment component (e.g., the aftertreatment component 140, 150) included in an aftertreatment system (e.g., the aftertreatment system 100, 200, 300, 400, 500), or an amount of ammonia in an exhaust gas flowing through the aftertreatment system using an optical assembly (e.g., the optical assembly 160, 260, 360).

The method 600 includes emitting light onto at least one of a face of the aftertreatment component, or through the exhaust gas, at 602. For example, the optical emitter 162 may emit light A onto the inlet face 141 or the outlet face 143 of the aftertreatment component 140, or onto the inlet face 151 or outlet face 153 of the upstream aftertreatment component 150. Alternatively or additionally, the optical emitter 262 may emit light A though the exhaust gas flowing through the aftertreatment system 400, 500.

At 604, at least one of light reflected from the face of the aftertreatment component, or light after passing through the exhaust gas is detected. For example, optical detector 164 may detect light B reflected from the corresponding face of the aftertreatment component 140, 150 and/or the optical detector 264 may detect light B after passing through the exhaust gas.

In some embodiments, an exhaust gas parameter may be determined, at 606. For example, the ammonia and NO amount determination circuitry 174b may be configured to receive one or more exhaust gas parameter signals from the engine 10, the first sensor 103 or the second sensor 105 and determine the exhaust gas parameters (e.g., exhaust gas temperature, pressure, flow rate, amount of $NO_x$ gases therein, etc.) At 608, an amount of ammonia and/or $NO_x$ on the corresponding face of the aftertreatment component, and/or an amount of ammonia in the exhaust gas is determined. For example, the ammonia and $NO_x$ amount determination circuitry 174b may be configured to interpret a detector signal received from the optical detector 164, 264 and determine the amount of ammonia and/or $NO_x$ on the corresponding face of the aftertreatment component 140, 150, and/or amount of ammonia in the exhaust gas based on an optical parameter (e.g., intensity) of the detected light. In some embodiments, the amount of ammonia in the exhaust gas is determined (e.g., by the ammonia and NO amount determination circuitry 174b) based on a difference between a parameter (e.g., a first intensity) of the light emitted from the optical emitter 162, 262 and a parameter (e.g., a second intensity) of the detected light that has reflected from the corresponding face of the aftertreatment component 140, 150, or has passed through the exhaust gas. In some embodiments, the difference may correspond to an absorbance, which corresponds to the amount of ammonia and/or NON.

In some embodiments, the exhaust gas parameters may be used to calibrate the optical parameter of the detected light. For example, various exhaust gas parameters such as temperature may impact the optical measurement. The portion of the optical parameter attributed to the variations in the exhaust gas parameter may be subtracted from the detector signal, or the optical parameter values may be normalized using one or more of the exhaust parameter value.

At 610, an amount of reductant inserted into the exhaust gas is adjusted. For example, the reductant insertion control circuitry 174c may selectively activate the reductant insertion assembly 120 to adjust an amount of reductant inserted into the exhaust gas based on the amount of ammonia and/or $NO_x$ gases on the corresponding face of the aftertreatment component 140, 150, or the amount of ammonia in the exhaust gas flowing through the aftertreatment system 100, 200, 300, 400, 500.

It should be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

As used herein, the term "about" generally mean plus or minus 10% of the stated value. For example, about 0.5 would include 0.45 and 0.55, about 10 would include 9 to 11, about 1000 would include 900 to 1100.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. An aftertreatment system configured to reduce constituents of an exhaust gas produced by an engine, comprising:
   an aftertreatment component;
   an optical assembly comprising:
      an optical emitter configured to emit light onto a face of the aftertreatment component, and
      an optical detector configured to detect light reflected from the face of the aftertreatment component; and
   a controller configured to determine at least one of an amount of $NO_x$ gases or an amount of ammonia on the face of the aftertreatment component based on an optical parameter of the detected light that has reflected from the face of the aftertreatment component.

2. The aftertreatment system of claim 1, wherein the controller is configured to determine the at least one of the amount of $NO_x$ gases or the amount of ammonia on the face of the aftertreatment component based on a difference between a parameter of the light emitted from the optical emitter and a parameter of the detected light that has reflected from the face of the aftertreatment component.

3. The aftertreatment system of claim 1, wherein the emitted light has a wavelength in the infrared (IR) range.

4. The aftertreatment system of claim 1, wherein the emitted light has a wavelength in the ultraviolet-visible (UV-vis) range.

5. The aftertreatment system of claim 1, wherein the face of the aftertreatment component is one of an inlet face structured to receive the exhaust gas, or an outlet face structured to expel exhaust gas.

6. The aftertreatment system of claim 5, wherein the aftertreatment component comprises a selective catalytic reduction catalyst.

7. The aftertreatment system of claim 1, further comprising:
   an upstream aftertreatment component disposed upstream of the aftertreatment component,
   wherein the aftertreatment component comprises an ammonia oxidation catalyst and the upstream aftertreatment component comprises a selective catalytic reduction catalyst.

8. The aftertreatment system of claim 1, wherein the optical emitter is disposed at a first location of the aftertreatment system, and the optical detector is disposed at a second location of the aftertreatment system that is opposite the first location.

9. The aftertreatment system of claim 1, wherein the controller is further configured to determine an amount of $NO_x$ gases and/or an amount of ammonia absorbed over an entire volume of the aftertreatment component based on the determined amount of $NO_x$ gases and/or ammonia on the face of the aftertreatment component.

10. The aftertreatment system of claim 9, further comprising:
    a reductant insertion assembly configured to insert a reductant into the exhaust gas flowing through the aftertreatment system,
    wherein the aftertreatment component comprises a selective catalytic reduction system, and
    wherein the controller is operatively coupled to the reductant insertion assembly, the controller further configured to, in response to determining that an amount of ammonia absorbed over the entire volume of the aftertreatment component is below an ammonia storage threshold, instruct the reductant insertion assembly to insert reductant into the exhaust gas.

11. The aftertreatment system of claim 10, wherein the controller is further configured to, in response to determining that an amount of $NO_x$ on the face of the aftertreatment component is above a $NO_x$ threshold, instruct the reductant insertion assembly to insert reductant into the exhaust gas.

12. The aftertreatment system of claim 9, further comprising:
    a reductant insertion assembly configured to insert a reductant into the exhaust gas flowing through the aftertreatment system,
    wherein the aftertreatment component comprises an ammonia oxidation catalyst, and wherein the controller is operatively coupled to the reductant insertion assembly, the controller further configured to, in response to determining that an amount of ammonia absorbed over the entire volume of the aftertreatment component is above an ammonia threshold, instruct the reductant insertion assembly to stop inserting reductant into the exhaust gas.

13. The aftertreatment system of claim 1, wherein the controller is further configured to calibrate an optical parameter value determined by the optical detector based on at least one of an exhaust gas temperature, an exhaust gas flow rate, an exhaust gas pressure, or an amount of water in the exhaust gas.

* * * * *